United States Patent [19]

Giacopuzzi

[11] Patent Number: 5,105,840
[45] Date of Patent: Apr. 21, 1992

[54] DENTAL FLOSS HOLDER

[76] Inventor: Guy G. Giacopuzzi, Lake Arrowhead Medical Center, Suite 208, P.O. Box 68, Cedar Glen, Calif. 92321

[21] Appl. No.: 523,974

[22] Filed: May 16, 1990

[51] Int. Cl.[5] ............................................. A61C 15/00
[52] U.S. Cl. .................................. 132/325; 132/326
[58] Field of Search ............... 132/322, 323, 324, 325, 132/326, 327

[56] References Cited

U.S. PATENT DOCUMENTS

| | | | |
|---|---|---|---|
| D. 251,074 | 2/1979 | Schiff | D28/64 |
| D. 251,075 | 2/1979 | Schiff | D28/64 |
| 1,110,680 | 9/1914 | Gamble | 132/325 |
| 1,627,525 | 5/1927 | Munro | 132/324 |
| 1,916,653 | 7/1933 | Bodde | 132/326 |
| 2,187,442 | 1/1940 | Beach | 132/326 |
| 2,217,917 | 10/1940 | Munro | 132/326 |
| 3,311,116 | 3/1967 | Foster | 132/326 |
| 3,792,706 | 2/1974 | Keese | 132/324 |
| 3,906,963 | 9/1975 | Jenkins et al. | 132/325 |
| 4,151,851 | 5/1979 | Bragg | 132/326 |
| 4,192,330 | 3/1980 | Johnson | 132/323 |
| 4,214,598 | 7/1980 | Lee | 132/325 |

Primary Examiner—Gene Mancene
Assistant Examiner—Michael Lynch
Attorney, Agent, or Firm—Pretty, Schroeder, Brueggemann & Clark

[57] ABSTRACT

A highly maneuverable dental floss holder has two centrally pivoted support members with holding sections extending on one side of the pivot and handle sections extending on the other side. Storage for new and used dental floss is provided between the handles. With single hand operation tension of the floss between the tips of the holding sections can be readily controlled and the dental floss can be selectively advanced.

10 Claims, 1 Drawing Sheet

DENTAL FLOSS HOLDER

BACKGROUND OF THE INVENTION

The benefits of using dental floss for removal of plaque from teeth have been known for many years. Daily flossing is recommended by almost all dentists. Nevertheless, because of the difficulty and inconvenience involved in manipulating the floss and the time delay of several minutes that is involved, very few people actually use dental floss on a daily basis.

Because of the difficulty of access to the back teeth, proper flossing is not an easy accomplishment. Initially the floss must be positioned in the space between two adjacent teeth. This positioning requires passing the floss through a narrow contact region between the teeth which is typically 0.25 to 1.25 millimeters deep. As the floss passes through this contact region, it encounters considerable resistance and must be drawn tight in order to provide sufficient force for passage through the contact region.

The intertooth space beneath the contact region is filled with a wedge shaped piece of soft tissue known as the gingival papilla. Care must be taken to assure that the floss does not suddenly "snap" through the contact region between the teeth while under tension and damage the gingival papilla between the teeth. Frequently bleeding of the gingival tissue is induced by traumatic contact with the floss as the floss snaps through the contact region.

To prevent this gingival damage the force on the dental floss must be reduced substantially just as the floss passes beneath the contact. This requires considerable dexterity and control. Once the floss is positioned beneath the contact, it should be allowed to partially wrap around the tooth to about 100 degrees of arc. It can then be passed between the papilla and one of the teeth as flossing proceeds.

Next the floss is moved to the adjacent tooth, still within the gap. The floss is now wrapped about the adjacent tooth and the flossing process is repeated before the floss is withdrawn from the intertooth gap. At this point the tension on the floss must again be increased as the floss is forced back through the contact region and out of the intertooth gap.

Studies have shown that the dental floss can transport bacteria from one quadrant of the mouth to another. In addition, waxed dental floss is frequently used to facilitate the flossing operation. The wax neither helps nor hinders the actual flossing operation, but does provide lubrication to make it easier to pass the floss through the contact region. However, the wax tends to come off the floss after two or three teeth have been flossed. It is therefore desirable to be able to store a supply of floss in the floss holder and advance a new length of floss to an active section at frequent intervals. At a minimum, the floss should be advanced for each different quadrant of the mouth.

Because floss is most conveniently available in standard 200 yard spools or reels, it is desirable that the floss holder be able to accommodate such a spool. It is further desirable that the floss holder provide storage for used floss. This enables the user to delay final disposal of the used floss to a time that is most convenient to the user.

One of the problems associated with flossing is the time required each day for proper flossing. However, this time requirement would be no problem if the flossing could be done while a person is engaged in some other confining activity, such as driving an automobile. This would of course require a holder that could be controlled with one hand to provide proper manipulation and tensioning as well as advancement of the floss from a supply spool to a take up mechanism.

Several different floss holder devices have been developed to assist in the flossing operation. However, none of these are able to satisfy all of the requirements of an ideal floss holder. For example, U.S. Pat. No. 1,110,680 to Gamble teaches a "scissor" type of floss holder. The holder provides looped type handles that are difficult to hold and do not facilitate proper control of floss position and tension. Two hands are required to advance the floss and there is no storage for used floss. The new floss supply mechanism cannot accommodate a standard 200 yard supply spool.

U.S. Pat. No. 4,192,330 to Johnson teaches a principle embodiment that uses a fixed cartridge. Once the cartridge is inserted, the floss is locked in tension without convenient adjustment. The cartridge must be replaced to obtain a new length of floss. Several such replacements would not be practical during a single flossing operation. In an alternative arrangement, a fixed length loop of floss is attached to the holder and then subjected to constant tension. The tension cannot be adjusted as appropriate for a proper flossing operation.

U.S. Pat. No. 3,792,706 to Keese discloses a holder in which a length of floss is secured to the ends thereof. In one embodiment the ends may be manipulated in response to finger pressure in order to change the tension. However, the control leverage arm is too short to provide adequate control over tension. In an alternative embodiment the holder arms can flex, but this cannot provide adequate control over floss tension.

U.S. Pat. No. 3,906,963 to Jenkins et al. teaches an arrangement in which a thumb screw can control the spacing between holder arms. Such a screw is too slow and inconvenient to represent a practical tooth by tooth adjustment. The floss is maintained under constant tension by a spring. No quick, convenient manual control of floss tension is provided.

U.S. Pat. No. 4,151,851 to Bragg teaches a holder having supply and take up reels on opposite sides thereof. The holder does not allow immediate manual control over floss tension and a long narrow handle makes precise positioning and control of the holder difficult.

U.S. Pat. No. 4,214,598 to Lee discloses supply and take up reels on a nonadjustable holder.

U.S. Pat. Des. 251,075 to Schiff and U.S. Pat. Des. 251,074 to Schiff show floss holders which use a fixed length of floss that cannot be advanced. The holder would appear to provide limited control over floss tension.

SUMMARY OF THE INVENTION

A convenient, precisely controllable dental floss holder in accordance with the invention can be easily held and properly manipulated with one hand. The holder includes a pair of generally straight parallel, spaced support members that are pivotably joined in a central region thereof in noncrossing relationship. A pair of support sections extend from the central region in one direction to terminate in a pair of spaced tips. A pair of hand sized handle sections that are approximately equal in length to the support sections extend from the control region in an opposite direction. Supply and take up mechanisms for dental floss are disposed between the handles.

A floss path is provided in the support members from the supply mechanism, past the spaced apart tips and then to the take up mechanism. The handle sections are shaped to conform to the shape of a user's hand. The spacing between the tips, and hence floss tension, is readily controlled by opening and closing the handles. Manual compression of the handles by squeezing tends to separate the tips to increase the tension on the floss. Relaxation of this force reduces the tension and allows the natural force of floss against a tooth to close the tips while opening the handles. Slack is thus provided to enable the floss to wrap part way around a tooth as it forms a "C" shape. Thumb force on the take up mechanism can be used concurrently with the gripping force to help control floss tension.

With single handed operation a user can tension the floss as it passes through the contact region between two teeth. As soon as the contact region is cleared by the floss, the hand may be relaxed somewhat to reduce floss tension and avoid damage to the gingival papilla. While the floss remains in the intertooth gap, the floss can be sequentially wrapped part way around each tooth adjacent to the gap as proper flossing action is completed. The floss can then be tightened by merely squeezing the hand as the floss passes back past the contact region for removal from the intertooth gap. Still with a single hand, the thumb may push against a take up spool to advance the floss and position a fresh length of floss between the tips.

BRIEF DESCRIPTION OF THE DRAWINGS

A better understanding of the invention may be had from a consideration of the following Detailed Description, taken in conjunction with the accompanying drawings in which.

DETAILED DESCRIPTION OF THE INVENTION

Figure 1:
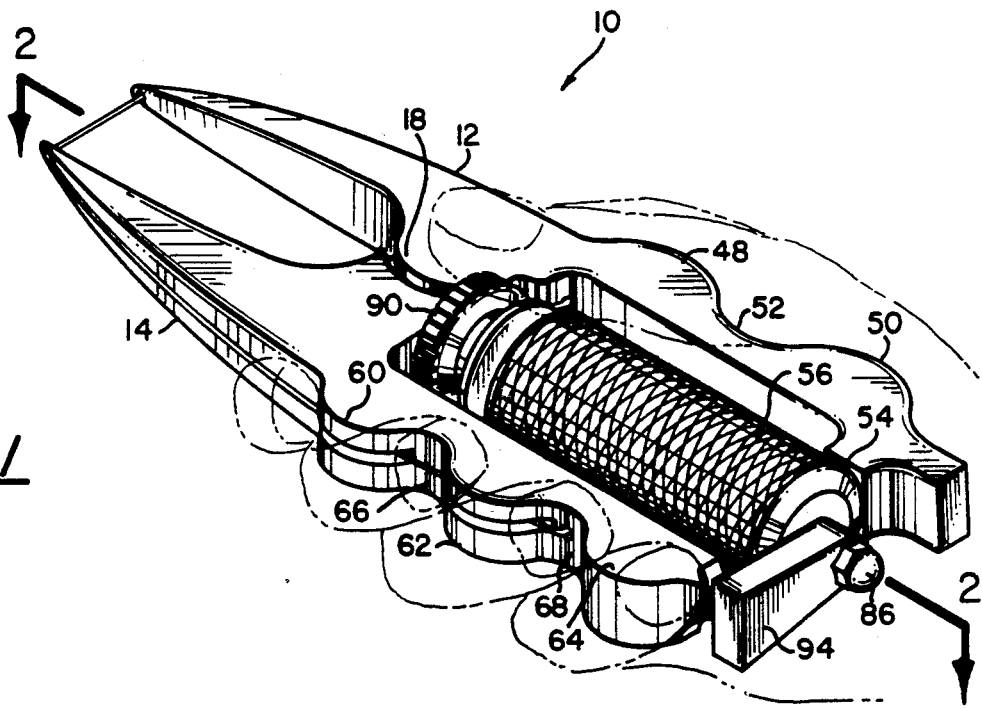
FIG. 1 is a perspective view of a dental floss holder in accordance with the invention.
Figure 2:
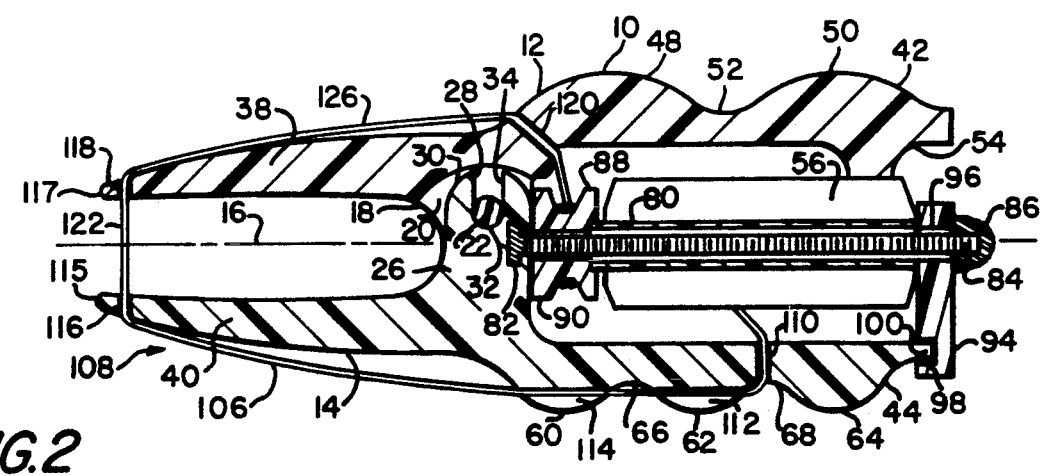
FIG. 2 is a sectional axis of the dental floss holder shown in FIG. 1.

Referring now to FIGS. 1 and 2 a single-handed, tension controllable dental floss holder 10 in accordance with the invention includes two elongated, substantially straight support members 12, 14 disposed in generally parallel opposed relationship on opposite sides of a longitudinally extending central axis 16. Support member 12 is intended to engage the thumb of a user while support member 14 is intended to engage the fingers of a user such that the holder 10 is conveniently held between the thumb and fingers of a single hand. A protrusion 18 is located approximately midway along the length of elongated support member 12 and extends inwardly toward the other support member 14 and central axis 16. Protrusion 18 has a longitudinally extending slot or recess 20 formed therein and a small cylindrical pivot pin 22 extends transversely across the slot 20.

Elongated support member 14 has a protrusion in the form of a mating tongue 26 that extends inwardly past central axis 16 toward elongated support member 12 where it is matingly received within the slot 20. Tongue 26 is somewhat narrower than the remainder of support member 14 in order that it may be accommodated within the slot 20. Tongue 26 further has a transversely extending recess 28 in the end 30 thereof that matingly receives the cylindrical pivot pin 22. Recess 28 has a cylindrical base 32 which is equal in diameter to pivot pin 22 and which matingly receives and retains the pivot pin 22. An outer portion 34 of recess 28 is slightly smaller than the diameter of pivot pin 22 such that pivot pin 22 upon assembly passes with a force fit through the outer portion 34 and snaps into place in mating relationship with the cylindrical base portion 32 to normally maintain the support members 12 and 14 in a pivotally connected relationship. The pivot pin 22 is spaced a short distance from central axis 16 toward the thumb side support member 12.

The support members 12, 14 extend in generally parallel, noncrossing relationship. The support members 12, 14 each have a holding section 38, 40 which extends on one side of the pivot pin 22 and a handle section 42, 44 which extends on the side of the pivot pin 22 opposite the holding sections 38, 40 respectively. The handle section 42 is shaped to comfortably mate in nonslip relationship with the base of a user's thumb and has two outwardly extending protrusions 48, 50 separated by an intermediate valley section 52. A stop 54 is provided in the form of a protrusion which extends inwardly from the support member 12 toward the support member 14. Upon engaging a supply reel of dental floss 56 the stop 54 limits the pivotable travel of the handle section 42 and further serves as a brake to prevent rotation of supply reel 56 when tension is applied to the floss. The handle section 44 of support member 14 has three outwardly extending protrusions 60, 62, 64 separated by intermediate valleys 66, 68 to comfortably receive the fingers of a user's hand and to provide a secure, non-slip grip. The large, hand sized handle sections 42, 44 combine with the protrusions and valleys thereon to enable the user to firmly hold the floss holder 10 in one hand in a firm and nonslip comfortable manner while the user asserts the necessary manipulations and forces to perform a dental flossing operation.

A shaft or spindle 80, which can be molded from plastic, has a fixed central end 82 secured to the inwardly projecting tongue 26 of support member 14 and extends along central axis 16. At least the distal end 84 of shaft 80 is threaded so as to receive in threaded relationship a tightening nut 86, which may also be made of plastic. The shaft 80 receives a rotatable take up reel 88 adjacent the central end 82 thereof and a rotatable supply reel of dental floss 56 outwardly of the take up reel 88. It will be appreciated that the relative locations of the take up reel 88 and supply reel 56 could be reversed. However, in the preferred embodiment the take up reel 88 is located inwardly of supply reel 56 so as to enable the thumb of a user to engage the outer periphery of take up reel 88 and manipulate the rotational position thereof so as to continually control floss tension during a flossing operation and also to easily advance the dental floss by rotating the take up reel while flossing proceeds. The exterior of take up reel 88 has a roughened or knurled flange 90 to facilitate non-slip engagement between a user's thumb and the take up reel 88. The nut 86 may be selectively tightened to control the force required to rotate supply reel 56 and take up reel 88.

A support member 94 has a cylindrical aperture 96 adjacent one end which receives the distal end of shaft 80 therethrough and a rectangular aperture or recess 98 adjacent an opposite end thereof. The distal end of handle section 44 terminates in a small rectangular cross sectioned shaft 100 which extends into and matingly engages the rectangular aperture or recess 98.

Support member 94 is readily removed by removing nut 86 and pulling support 94 from shaft 80 and shaft 100. The supply reel of dental floss 56 is thus fully released and may be selectively removed and replaced with a fresh reel of dental floss. Support member 94 is then replaced with aperture 96 receiving the distal end of shaft 80 and cavity 98 receiving the distal end of shaft 100. Nut 86 may then be tightened on the distal end 84 of shaft 80 to secure support member 94 in place and force support member 94 and supply reel 56 forward toward the central or pivot region of holder 10. By controlling the tightness of nut 86 a user can selectively control the forces required to rotate take up reel 88 and supply reel 56 relative to the holder 10. Support member 94 serves to support the distal end 84 of shaft 80 and in particular supports the shaft against substantial forces which may be applied by stop 50 engaging supply reel 56 when the handle sections 42, 44 are squeezed together by a user.

A dental floss path is defined from the supply reel 56 past the tips 115, 117 of the support members 44, 42 and back to the take up reel 88. A hole 110 is drilled through the handle section 44 of support member 14 in the vicinity of valley 68 which is positioned approximately midway along the axial length of supply reel 56. Slots 112, 114 are formed in protrusions 62, 60 respectively and a hole 116 is formed in the tip or distal end 115 of holding section 40 of support member 14. The path continues across to a hole 118 in the tip or distal end 117 of holding section 38 of support member 12 and then through a hole 120 in the handle section 48 of support member 12 near the center pivot of support member 12 and in juxtaposition with the take up reel 88. The floss path thus extends from supply reel 56 through hole 110, through slots 112, 114 in the handle of support member 14, and then through hole 116 in the tip 115 of support member 14. From the tip 115 of support member 14 the path extends across to the tip 117 of support member 12 where it passes through a hole 118 and then extends back toward the handle section 48 to pass through hole 120 and be wound upon the take up reel 88. For the preferred embodiment the floss is secured to reel 88 by merely winding two or three turns of floss thereon until a nonslip engagement is secured between the floss and the reel 88. However, a transverse slot or other device may be used to more positively secure an end of a length of floss to take up reel 88 if desired. In practice this has not been found to be necessary.

During use, the user closes the handles 42, 44 to spread the tips and force stop 54 against the supply reel 56. The user's thumb is asserted against take up reel 88 to tighten the floss 106 along the floss path 108. An active length of floss 12 between the holder tips is then positioned in the mouth opposite a tooth contact and, with the floss 106 held in tension, is forced through the intertooth contact. As the active length 122 passes through the intertooth contact, the grip may be relaxed to allow the tips to move closer together and provide slack at the active length of floss 122. At the same time the thumb grip on reel 88 may be relaxed to further increase the length of active floss in section 122 to permit the floss to wrap part way around the tooth inside of the gingival papilla to form a C-shaped partial loop about the tooth. Flossing may then proceed. Flossing is then repeated for the adjacent tooth before the grip is tighten and the thumb hold on take up reel 88 is tighten to increase the tension on the active length of floss 122 and remove the floss from the intertooth contact. If desired, a fresh length of floss may now be advanced to the active length of floss 122 between the holder tips before flossing the next intertooth cavity. This floss advancement may be accomplished while continuing single hand manipulation of the holder 10 by merely relaxing the grip so as to release stop 54 from supply reel 56 while rotating the take up reel 88 with the thumb.

Studies have shown that it is desirable to advance the active length of floss 122 at least for each separate quadrant of the mouth so as to preclude a contaminated section of floss 106 from acting as a carrier of infection from one quadrant of the mouth to another. If this is not done the floss may pick up bacteria at one intertooth contact cavity and spread the bacteria to another noninfected cavity. In addition, most people prefer to use a waxed type of dental floss. The wax does not aid or improve the flossing activity itself, but does act as a lubricant to enable the active length of floss 122 to more readily negotiate the contact region between adjacent teeth. The wax tends to wear off after two or three contacts have been negotiated and it is therefore desirable to frequently advance the floss 106 so that a freshly waxed length of floss lies between the two tips at all times. The holder 10 not only provides a convenient and comfortable holding for proper flossing operations, but also enables one handed manipulation of the holder 10 to easily and quickly advance a length of floss so that a fresh length of floss is readily provided to the active length of floss 122.

The take up reel 88 has a much smaller capacity then the supply reel 56. However, the take up reel 88 has sufficient capacity for about 30 flossings. Any time it is desired to empty the take up reel, the floss is simply cut at a suitable location such as at a cut point 126 along the support section 38 of holder 12. The newly freed end of used floss is then pulled until all floss has been removed from the take up reel 88. If desired, the nut 86 can be loosened slightly to allow reel 88 to turn more freely and then retightened after the used floss has been removed. The cut end of floss 106 is then passed through the remainder of floss path 108 and wound upon take up reel 88 until properly secured thereto.

While there has been shown and described above a particular arrangement of a single handed, easily controlled floss holder in accordance with the invention for the purpose of enabling a person of ordinary skill in the art to make and use the invention, it will be appreciated that the invention is not limited thereto. Accordingly, any modifications, variations or equivalent arrangements within the scope of the attached claims should be considered to be within the scope of the invention.

What is claimed is:

1. A dental floss holder comprising a pair of centrally pivotally connected support members having opposed handle sections and opposed support sections which each terminate at a tip; a pivot pin providing pivotal coupling between the pair of support members; a take up reel disposed between the handle sections; a shaft adapted to receive and support a supply reel of dental floss disposed between the handle sections; the support members having defined therein a floss path from the shaft past the tips of the support sections and to the take up reel; and wherein the take up reel is rotatably mounted on the shaft adjacent the pivot pin.

2. A dental floss holder according to claim 1 wherein the floss path includes a hole through the tip of each support member that is sufficiently large to pass floss therethrough.

3. A dental floss holder according to claim 1 wherein the shaft is sufficiently long to support the take up reel and a supply reel containing 200 yards of dental floss.

4. A dental floss holder according to claim 1 further comprising a supply reel of dental floss rotatably mounted on the shaft.

5. A dental floss holder according to claim 4 wherein the supply reel has sufficient capacity to store 200 yards of dental floss.

6. A dental floss holder according to claim 1 wherein the handle sections are sculptured to provide comfortable, nonslip, one handed gripping and operation of the dental floss holder.

7. A dental floss holder comprising:
   first elongated support member having a pivot point, a holding section extending from the pivot point on one side thereof to a tip and a handle section extending from the pivot point in a direction opposite the holding section;
   a second elongated support member having a pivot point, a holding section extending from the pivot point on one side thereof to a tip and a handle section extending from the pivot point in a direction opposite the holding section, the first and second support members being pivotably connected in noncrosssing relationship at the respective pivot points with the holding sections and handle sections being in respective opposed, spaced relationship;
   a shaft secured to the second elongated support member and extending between the handle sections of the first and second support members; and
   a take up reel disposed on the shaft for rotation thereabout, the shaft being sufficiently long to rotatably receive and support a supply reel containing dental floss in addition to the take up reel and the first and second elongated support members defining a path for passage of dental floss from the supply reel past the tips of holding sections of the first and second support members and then to the take up reel.

8. A dental floss holder comprising:
   a pair of elongated support members extending in generally parallel spaced relationship, the support members being pivotably connected together at a central region thereof, each support member having a holding section extending from the central region to a tip and having a handle section extending from the central region in a direction opposite the holding section, the support members being pivotably connected together in a noncrossing relationship such that compression of the handle sections closer together tends to spread the tips farther apart, the support members defining a path for passage of dental floss from a supply region between the handle sections past the tips and then to a take up region between the handle sections, one of the support members being adapted to frictionally engage a supply of dental floss in the supply region and thereby preclude advancement of dental floss to the holding sections of the support members;
   a supply mechanism disposed between the handle sections in the supply region to receive and support a supply of dental floss; and
   a take up mechanism disposed in the take up region between the handle sections to receive used dental floss, the take up region being between the supply region and the pivot point; the handle sections being adapted to be held within a single hand and the take up mechanism being adapted to be manipulated by at least one of a thumb and forefinger of the single hand such that the take up mechanism can be selectively manipulated to control tension of dental floss past the holding sections to the supply mechanism to control dental floss length and tension between the holding sections while frictional engagement between the one support member and the supply mechanism is controlled to selectively allow advancement of the dental floss from the supply mechanism to the take up mechanism.

9. A dental floss holder according to claim 8 wherein the take up mechanism is a reel disposed to be selectively rotated between a thumb and forefinger of a hand holding the handle sections.

10. A dental floss holder according to claim 9 wherein the supply mechanism includes a reel of dental floss.

* * * * *

UNITED STATES PATENT AND TRADEMARK OFFICE
CERTIFICATE OF CORRECTION

PATENT NO. : 5,105,840
DATED : 4/21/92
INVENTOR(S) : Guy Giacopuzzi

It is certified that error appears in the above-identified patent and that said Letters Patent is hereby corrected as shown below:

In column 3, line 41, change "sectional axis" to --sectional view taken through a central longitudinal axis--.

In column 5, line 55: change "floss 12" to --floss 122--.

In column 5, line 68: change "tighten and the thumb hold on take up reel 88 is tighten" to --tightened and the thumb hold on take up reel 88 is tightened".

Signed and Sealed this

Twenty-ninth Day of June, 1993

Attest:

MICHAEL K. KIRK

*Attesting Officer*  Acting Commissioner of Patents and Trademarks